(12) United States Patent
Moriwaki et al.

(10) Patent No.: US 9,095,156 B2
(45) Date of Patent: Aug. 4, 2015

(54) OIL OR FAT COMPOSITION

(75) Inventors: Junya Moriwaki, Sumida-ku (JP); Masao Shimizu, Sumida-ku (JP); Rika Homma, Sumida-ku (JP)

(73) Assignee: KAO CORPORATION, Tokyo (JP)

( * ) Notice: Subject to any disclaimer, the term of this patent is extended or adjusted under 35 U.S.C. 154(b) by 194 days.

(21) Appl. No.: 13/638,865

(22) PCT Filed: Feb. 25, 2011

(86) PCT No.: PCT/JP2011/054304
§ 371 (c)(1),
(2), (4) Date: Oct. 1, 2012

(87) PCT Pub. No.: WO2011/122188
PCT Pub. Date: Oct. 6, 2011

(65) Prior Publication Data
US 2013/0023684 A1    Jan. 24, 2013

(30) Foreign Application Priority Data
Mar. 31, 2010    (JP) .................................. 2010-083158

(51) Int. Cl.
*C11C 3/00*      (2006.01)
*A23D 9/007*    (2006.01)
*A61Q 19/00*    (2006.01)
*A23D 7/005*    (2006.01)
*C07C 57/03*    (2006.01)

(52) U.S. Cl.
CPC .............. *A23D 9/007* (2013.01); *A23D 7/0053* (2013.01); *A23D 7/0056* (2013.01); *A61Q 19/00* (2013.01); *C11C 3/00* (2013.01); *C07C 57/03* (2013.01)

(58) Field of Classification Search
CPC ...................................................... A23D 9/00
USPC .......................................... 426/607; 554/227
See application file for complete search history.

(56) References Cited

U.S. PATENT DOCUMENTS

| | | |
|---|---|---|
| 4,599,143 A | 7/1986 | Stage |
| 4,601,790 A | 7/1986 | Stage |
| 2008/0069932 A1 | 3/2008 | Kohori et al. |

FOREIGN PATENT DOCUMENTS

| | | |
|---|---|---|
| CN | 1949983 A | 4/2007 |
| EP | 1 746 149 A1 | 1/2007 |
| JP | 59 68398 | 4/1984 |
| JP | 62-205738 A | 9/1987 |
| JP | 11-196766 A | 7/1999 |
| JP | 2009-284824 A | 12/2009 |
| JP | 2011 74358 | 4/2011 |
| JP | 2011 213835 | 10/2011 |
| JP | 2011 213856 | 10/2011 |

OTHER PUBLICATIONS

Franke, K., et al., Influence of chemical refining process and oil type on bound 3-chloro-1,2-propanediol contents n palm oil and rapeseed oil, 2009, LWT—Food Science and Technology, vol. 42, pp. 1751-1754.*
Larsen, J. C., 3-MCPD esters in food products, 2009. International Live Science Institute, Summary Repor of a workshop held in Brussels, Belgium, 36 pages.*
U.S. Appl. No. 13/996,904, filed Jun. 21, 2013, Homma, et al.
Weisshaar, R., et al., "Fatty acid esters of glycidol in refined fats and oils," European Journal of Lipid Science and Technology, vol. 112, No. 2, pp. 158 to 165, (Feb. 2010).
Bauer, N., "Glycidol-Fettsaeureester in Saeuglingsmilchnahrung nachgewiesen," DLR, vol. 105, No. 6, pp. 361 to 362, (Jun. 2009).
International Search Report Issued May 31, 2011 in PCT/JP11/54304 Filed Feb. 25, 2011.
U.S. Appl. No. 13/988,170, filed May 17, 2013, Homma, et al.
Li Weiwen, "A Brief Research on the Methods of Determinating Hydroxyl Value and its Related Factors", Journal of Suzhou Institute of Silk Textile Technology, vol. 17, No. 5, Oct. 31, 1997, pp. 27-30 (with English abstract of p. 30).
The Cabinet Office Food Safety Commission of Japan, A Comprehensive Study for Ensuring Food Safety for the year 2006, "A Basic Survey Report on Assessment of Trans Fatty Acids in Foods", Japan Food Research Labolatories, Mar. 2007, pp. 1-45 (with partial English translation).
Kao Corporation, Food additives (emulsifier preparation) EXCEL O-95R (EXCEL O-95R)(purely vegetable molecular distillation monoglyceride), Chemical Business Unit, 1999, pp. 1-2 (with computer generated English translation).
U.S. Appl. No. 14/240,214, filed Feb. 21, 2014, Homma, et al.
U.S. Appl. No. 14/347,888, filed Mar. 27, 2014, Homma, et al.
U.S. Appl. No. 14/347,915, filed Mar. 27, 2014, Homma, et al.
U.S. Appl. No. 14/240,295, filed Feb. 21, 2014, Homma, et al.
U.S. Appl. No. 14/240,206, filed Feb. 21, 2014, Homma, et al.
U.S. Appl. No. 14/240,248, filed Feb. 21, 2014, Homma, et al.
U.S. Appl. No. 14/240,209, filed Feb. 21, 2014, Homma, et al.
U.S. Appl. No. 14/350,955, filed Apr. 10, 2014, Homma.

* cited by examiner

*Primary Examiner* — Yate K Cutliff
(74) *Attorney, Agent, or Firm* — Oblon, McClelland, Maier & Neustadt, L.L.P.

(57) ABSTRACT

Provided is an oil or fat composition, which has an MCPD-FS content X (ppm) and a hydroxyl value Y (mg-KOH/g) satisfying a relationship of the following expression (1), the content X being measured by a Deutsche Gesellschaft für Fettwissenschaft (DGF) standard method C-III 18(09), and has a content (%) of trans isomers of linoleic acids in constituent fatty acids of an oil or fat, of 2 or more.

$Y \geq 1.25X+4$ where $Y \leq 88$      (1).

19 Claims, No Drawings

OIL OR FAT COMPOSITION

FIELD OF THE INVENTION

The present invention relates to an oil or fat composition having an improved taste and flavor.

BACKGROUND OF THE INVENTION

An oil or fat is essential as a nutrient and energy source for a body (primary function), and moreover, is important for providing the so-called sensory function (secondary function), which satisfies preference such as a taste and an aroma. In addition, an oil or fat containing diacylglycerols at a high concentration is known to have a physiological action (tertiary function) such as a body fat-burning action.

An untreated oil or fat obtained by squeezing seeds, germs, pulp or the like of a plant contains, for example, fatty acids, monoacylglycerols, odor components or the like. Further, when an oil or fat is subjected to a heating process by using a transesterification reaction, an esterification reaction, hydrogenation treatment or the like, trace components are produced in the oil or fat, and thus the taste and flavor of the oil or fat is impaired. In order to use such oil or fat as edible oil, the taste and flavor thereof needs to be improved by removing these trace components. The so-called deodorization treatment in which an oil or fat is brought into contact with water vapor at high temperature under reduced pressure is generally carried out as means for removing the trace components (Patent Document 1).

PRIOR ART DOCUMENT

Patent Document

[Patent Document 1]: JP-A-59-68398

SUMMARY OF THE INVENTION

The present invention relates to the following items 1) to 14).
1) An oil or fat composition, which has an MCPD-FS content $X$ (ppm) and a hydroxyl value $Y$ (mg-KOH/g) satisfying a relationship of the following expression (1), the content $X$ being measured by a Deutsche Gesellschaft für Fettwissenschaft (DGF) standard method C-III 18 (09), and has a content (%) of trans isomers of linoleic acids in constituent fatty acids of an oil or fat, of 2 or more.

$$Y \geq 1.25X+4 \text{ (where } Y \leq 88\text{)} \tag{1}$$

2) The oil or fat composition according to the above-mentioned item 1), which has a hydroxyl value $Y$ of 4.9 to 88 mg-KOH/g.
3) The oil or fat composition according to the above-mentioned item 1), which has a hydroxyl value $Y$ of 19 to 87 mg-KOH/g.
4) The oil or fat composition according to the above-mentioned item 1), wherein the MCPD-FS content $X$ (ppm) and the hydroxyl value $Y$ (mg-KOH/g) satisfy a relationship of the following expression (2), the content $X$ being measured by the Deutsche Gesellschaft für Fettwissenschaft (DGF) standard method C-III 18 (09).

$$Y \geq 2X+4 \text{ (where } Y \leq 70.5\text{)} \tag{2}$$

5) The oil or fat composition according to the above-mentioned item 1) or 4), which has a hydroxyl value $Y$ of 26 to 70 mg-KOH/g.
6) The oil or fat composition according to any one of the above-mentioned items 1) to 5), which has an MCPD-FS content (ppm) of 10 ppm or less, the content being measured by the Deutsche Gesellschaft für Fettwissenschaft (DGF) standard method C-III 18(09).
7) The oil or fat composition according to any one of the above-mentioned items 1) to 5), which has an MCPD-FS content (ppm) of 9 ppm or less, the content being measured by the Deutsche Gesellschaft für Fettwissenschaft (DGF) standard method C-III 18(09).
8) The oil or fat composition according to any one of the above-mentioned items 1) to 5), which has an MCPD-FS content (ppm) of 5 ppm or less, the content being measured by the Deutsche Gesellschaft für Fettwissenschaft (DGF) standard method C-III 18(09).
9) The oil or fat composition according to any one of the above-mentioned items 1) to 5), which has an MCPD-FS content (ppm) of 0.1 to 5 ppm, the content being measured by the Deutsche Gesellschaft für Fettwissenschaft (DGF) standard method C-III 18(09).
10) The oil or fat composition according to any one of the above-mentioned items 1) to 5), which has an MCPD-FS content (ppm) of 0.4 to 4.7 ppm, the content being measured by the Deutsche Gesellschaft für Fettwissenschaft (DGF) standard method C-III 18(09).
11) The oil or fat composition according to any one of the above-mentioned items 1) to 10), which has a content ratio (%) of trans isomers of linoleic acids in constituent fatty acids of an oil or fat, of 2 to 8.
12) The oil or fat composition according to any one of the above-mentioned items 1) to 10), which has a content ratio (%) of trans isomers of linoleic acids in constituent fatty acids of an oil or fat, of 2 to 5.
13) The oil or fat composition according to any one of the above-mentioned items 1) to 10), which has a content ratio (%) of trans isomers of linoleic acids in constituent fatty acids of an oil or fat, of 2.1 to 5.
14) The oil or fat composition according to any one of the above-mentioned items 1) to 10), which has a content ratio (%) of trans isomers of linoleic acids in constituent fatty acids of an oil or fat of, 2.1 to 2.6.

EMBODIMENT FOR CARRYING OUT THE INVENTION

The above-mentioned deodorization treatment is usually carried out at high temperature and the treatment distills and removes odor components, resulting in an oil or fat having a good taste and flavor. On the other hand, the inventors of the present invention have found the problem that something having a slightly heavy taste and flavor is produced in an oil or fat composition obtained by the deodorization treatment carried out at high temperature, in addition to the odor components that are removed through the deodorization treatment. This phenomenon occurs more remarkably in an oil or fat composition having a thermal history of higher temperature. Further, the inventors have also found that changing conditions of deodorization treatment does not always result in producing an oil or fat composition having a good taste and flavor.

Note that, in this description, the phrase "heaviness of a taste and flavor" of an oil or fat composition refers to a "viscous and sticking sense in the mouth" and is also expressed as an "oily taste."

The inventors of the present invention have made studies on the problem that something having a slightly heavy taste and flavor is produced in the above-mentioned oil or fat composition with a certain thermal history. As a result, the inventors of the present invention have found that the content of MCPD-FS (3-monochloro-1,2-propanediol forming substances—including 3-monochloro-1,2-propanediol, 3-monochloropropane-1,2-diol fatty acid esters, glycidol, and glycidol fatty acid esters) measured by a Deutsche Gesellschaft fair Fettwissenschaft (hereinafter, also referred to as "DGF") standard method C-III 18(09) is increased in the oil or fat composition, and that the content (ppm) of the MCPD-FS in the oil or fat composition has a high correlation with the above-mentioned "slightly heavy taste and flavor". Further, the inventors of the present invention have found that, when the hydroxyl value of an oil or fat composition is larger than a value calculated by substituting the MCPD-FS content (ppm) in the oil or fat composition into a certain expression, the oil or fat composition has an excellent taste and flavor. Note that heating causes the isomerization of double bonds in unsaturated fatty acids of an oil or fat, resulting in the increase of the generation of trans isomers. Hence, the inventors of the present invention used the content ratio of trans isomers as an index of the thermal history of an oil or fat composition.

According to the present invention, an oil or fat composition having an excellent taste and flavor is provided.

The oil or fat composition according to the present invention may be produced from any of a vegetable oil or fat and an animal oil or fat as a raw material. Specific examples of the raw material include vegetable oils or fats such as soybean oil, rapeseed oil, safflower oil, rice bran oil, corn oil, palm oil, sunflower oil, cotton seed oil, olive oil, sesame oil, and perilla oil, animal oils or fats such as fish oils, lard, beef tallow, and butter fat, and oils or fats such as transesterified oils, hydrogenated oils, and fractionated oils thereof.

The oil or fat composition according to the present invention contains one or more kinds of monoacylglycerols, diacylglycerols, and triacylglycerols. The content of monoacylglycerols in the oil or fat composition is preferably 0 to 30 mass % (hereinafter, simply referred to as "%"), more preferably 0.1 to 28%, even more preferably 0.2 to 25%, even more preferably 0.5 to 20%, from the viewpoint that the oil or fat composition has a better taste and flavor. The content of diacylglycerols in the oil or fat composition is preferably 2 to 95%, more preferably 3 to 90%, even more preferably 4 to 50%, even more preferably 5 to 20%, from the viewpoints of its physiological effects and the industrial productivity of an oil or fat. The content of triacylglycerols is preferably 5 to 98%, more preferably 9.9 to 96.9%, even more preferably 49.8 to 95.8%, even more preferably 75 to 94.5%, from the viewpoint of the industrial productivity of an oil or fat.

The constituent fatty acids of an oil or fat in the oil or fat composition according to the present invention are not particularly limited, and any of saturated fatty acids and unsaturated fatty acids may be used. Unsaturated fatty acids account for preferably 80 to 100% of the constituent fatty acids, more preferably 90 to 100%, even more preferably 93 to 100%, even more preferably 93 to 98%, even more preferably 94 to 98%, from the viewpoints of the outer appearance of the resulting oil or fat composition and the industrial productivity of the oil or fat. The number of carbons in the unsaturated fatty acids is preferably 14 to 24, more preferably 16 to 22 from the viewpoint of the physiological effects of the oil or fat composition.

Naturally-occurring unsaturated fatty acids having double bonds, which generally have cis conformations, may undergo isomerization to a trans form owing to the thermal history thereof. In the constituent fatty acids of an oil or fat in the oil or fat composition according to the present invention, the content of trans-oleic acid, that is, elaidic acid, is preferably 1% or less, more preferably 0.5% or less, even more preferably 0.3% or less, from the viewpoint of the physiological effects thereof.

Further, in the constituent fatty acids of an oil or fat in the oil or fat composition, the content of saturated fatty acids is preferably less than 20%, more preferably 0 to 10%, even more preferably 0 to 7%, even more preferably 2 to 7%, even more preferably 2 to 6%, from the viewpoints of its outer appearance, its physiological effect, and the industrial productivity of the oil or fat. The saturated fatty acids have preferably 14 to 24 carbon atoms, more preferably 16 to 22 carbon atoms.

The oil or fat composition according to the present invention has an MCPD-FS content X (ppm) and a hydroxyl value Y (mg-KOH/g) satisfying a relationship of the following expression (1), the content X being measured by a Deutsche Gesellschaft für Fettwissenschaft (DGF) standard method C-III 18(09).

$$Y \geq 1.25X+4 \text{ (where } Y \leq 88) \tag{1}$$

In addition, X and Y preferably satisfy a relationship of the following expression (2).

$$Y \geq 2X+4 \text{ (where } Y \leq 70.5) \tag{2}$$

As described previously, an oil or fat composition with a certain thermal history has an increased MCPD-FS content (ppm) and has a heavy taste and flavor. Further, the degree of the thermal history of an oil or fat composition is reflected in the content of trans-unsaturated fatty acids in the oil or fat composition. Thus, when the ratio of fatty acids having two double bonds including a trans double bond and having 18 carbon atoms (referred to as "trans-linoleic acids") to fatty acids having two double bonds and having 18 carbon atoms (referred to as "all linoleic acids") is expressed in terms of percentage (the ratio being referred to as "content ratio (%) of trans isomers" or "LTR"), the present invention aims at providing an oil or fat composition having a value equal to or higher than a certain value of LTR. The value of LTR is preferably 2 or more, more preferably 2 to 8, even more preferably 2 to 5, even more preferably 2.1 to 5, even more preferably 2.1 to 2.6, from the viewpoint that the effects of the present invention are exerted effectively.

In the present invention, MCPD-FS may be measured by the Deutsche Gessellschaft für Fettwissenschaft (DGF) standard method C-III 18 (09) (DGF Standard Methods 2009 (14. Supplement), C-III 18 (09), "Ester-bound 3-chloropropane-1,2-diol (3-MCPD esters) and glycidol (glycidyl esters)").

The DGF standard method C-III 18 (09) is a microanalytical method for an oil or fat using a gas chromatograph-mass spectrometer (GC-MS) and is a measurement method for 3-chloropropane-1,2-diol and esters thereof (MCPD esters), and glycidol and esters thereof.

The total content of these four components is measured as an analytical value of MCPD-FS.

In the present invention, a method described in option A ("7.1 Option A: Determination of the sum of ester-bound 3-MCPD and glycidol") described in the standard method 7.1. is employed. The details of the measurement method are described in Examples.

The MCPD-FS content in the oil or fat composition according to the present invention is preferably 10 ppm or less, more preferably 9 ppm or less, more preferably 5 ppm or less, more preferably 0.1 to 5 ppm, even more preferably 0.4 to 4.7 ppm, from the viewpoint of improving the heaviness of its taste and flavor.

The oil or fat composition according to the present invention has a hydroxyl value Y of preferably 88 mg-KOH/g or less, and has a hydroxyl value of more preferably 4.9 to 88 mg-KOH/g, even more preferably 19 to 87 mg-KOH/g, even more preferably 26 to 70 mg-KOH/g, from the viewpoint of improving the heaviness of its taste and flavor.

Herein, the hydroxyl value refers to a value obtained by measurement in accordance with "Hydroxyl value (pyridine-acetic anhydride method 2.3.6.2-1996)" in "Standard Methods for the Analysis of Fats, Oils and Related Materials, 2003" edited by Japan Oil Chemists' Society.

The details of the measurement method for the hydroxyl value are described in Examples.

The hydroxyl value of the oil or fat composition may be controlled by appropriately combining, in addition to various kinds of oils or fats, monoacylglycerols or diacylglycerols, organic acid monoglycerides, and polyol fatty acid esters such as polyglycerin condensed licinoleic acid esters, polyglycerin fatty acid esters, sucrose fatty acid esters, sorbitan-fatty acid esters, polyoxyethylene sorbitan fatty acid esters, and propylene glycol fatty acid esters, so that the hydroxyl value falls within the above-mentioned range.

A refinement step that is generally used for an oil or fat may be used as a refinement step of the oil or fat composition according to the present invention. More specifically, it includes a top cut distillation step, an acid treatment step, a decoloration step, a water washing step, a deodorization step, and a thin-film evaporation treatment step or the like.

The top cut distillation step refers to the step of distilling an oil or fat composition, thereby removing light by-products such as fatty acids from it.

The acid treatment step refers to a step including adding a chelating agent such as citric acid to an oil or fat, followed by their mixing, and then subjecting the resulting mixture to oil-water separation or dehydration under reduced pressure to remove water, thereby removing impurities. An amount of the chelating agent to be used is preferably 0.001 to 5%, more preferably 0.01 to 1%, with respect to the oil or fat.

The decoloration step refers to a step including bringing an adsorbent or the like into contact with an oil or fat, thereby additionally improving its color and its taste and flavor. A porous adsorbent is preferably used as the adsorbent, and examples thereof include activated carbon, silicon dioxide, and a solid acid adsorbent. Examples of the solid acid adsorbent include acid clay, activated clay, activated alumina, silica gel, silica/alumina, and aluminum silicate or the like. The adsorbent may be used alone, or two or more kinds adsorbents may be used in combination. Of those, a solid acid adsorbent is preferred, and acid clay and activated clay are more preferred, from the viewpoint of reducing the content of by-products and the viewpoint of improving the taste and flavor and the color. An amount of the adsorbent to be used is preferably less than 2%, more preferably 0.1% to less than 2%, more preferably 0.2 to 1.5%, even more preferably 0.3 to 1.3%, with respect to the oil or fat from the viewpoint of additionally improving the color and the taste and flavor and the viewpoint of increasing the productivity.

The water washing step refers to a step including bringing water into contact with an oil or fat, thereby performing oil-water separation. Water washing can remove water-soluble impurities. The water washing step is preferably repeated a plurality of times (for example, three times).

The deodorization step is a step including applying steam distillation under reduced pressure to an oil or fat. Examples of the temperature condition in the step include preferably 120 to 270° C., more preferably 175 to 250° C., even more preferably 220 to 230° C. Examples of the treatment time in the step include preferably 1 to 300 minutes, more preferably 3 to 180 minutes, even more preferably 5 to 110 minutes. Further, in an embodiment of the present invention, it is preferred to combine deodorization treatments under the condition of a thermal history of lower temperature (milder condition) than that of usual deodorization treatment, in the final step of refining treatment, from the viewpoint of improving its taste and flavor. In this case, the combined condition of the temperature and treatment time in usual deodorization treatment is 190 to 220° C. and 120 to 300 minutes, 220 to 250° C. and 30 to 180 minutes, 250 to 270° C. and 5 to 60 minutes, or the like.

On the other hand, the conditions of the deodorization treatment having a thermal history of lower temperature include: preferably a treatment temperature of 120 to 230° C., more preferably a lower limit temperature of 175° C. in addition to the foregoing condition; preferably a treatment time of 1 to 110 minutes, more preferably a lower limit time of 5 minutes in addition to the foregoing condition; a pressure of preferably 0.02 to 2 kPa, more preferably 0.03 to 1 kPa; and an amount of water vapor or the like of preferably 0.1 to 100, more preferably 0.5 to 6%, with respect to the amount of an oil or fat subjected to the deodorization treatment.

In particular, from the viewpoint of improving the taste and flavor of an oil or fat, (A) when its treatment temperature is 120° C. or more and 205° C. or less, its treatment time is preferably 5 to 110 minutes, more preferably 15 to 70 minutes, (B) when its treatment temperature is more than 205° C. and 215° C. or less, its treatment time is preferably 5 to 50 minutes, more preferably 8 to 45 minutes, even more preferably 12 to 40 minutes, and (C) when its treatment temperature is more than 215° C. and 230° C. or less, its treatment time is preferably 5 to 30 minutes, more preferably 7 to 27 minutes, even more preferably 10 to 24 minutes.

The thin-film evaporation treatment step refers to a treatment in which a material for distillation is formed into a thin film, followed by heating, thereby evaporating a light cut fraction from an oil or fat, thus yielding the treated oil or fat as a residual fraction. The treatment is carried out by using a thin-film evaporator. The thin-film evaporator includes a centrifugal thin-film distillation apparatus, a falling film distillation apparatus, and a wiped film evaporator (wiped film distillation) or the like, which are different depending on methods of forming a thin film.

An antioxidant may be further added to the oil or fat composition according to the present invention as is the case with common edible oil or fat, from the viewpoints of improving its storage stability and the stability of its taste and flavor. The antioxidant includes natural antioxidants, tocopherol, ascorbyl palmitate, ascorbyl stearate, BHT, BHA, and phospholipids or the like.

The oil or fat composition according to the present invention may be used in exactly the same applications as a general edible oil or fat, and may be widely applied to various foods and drinks in which an oil or fat is used. The oil or fat composition according to the present invention may be used for, for example: oil-in-water type oil or fat processed foods such as drink, dessert, ice cream, dressing, toppings, mayonnaise, and sauce for grilled meat; water-in-oil type oil or fat processed foods such as margarine and spread; processed oil or fat foods such as peanut butter, frying shortening, and baking shortening; processed foods such as potato chips, snacks, cake, cookies, pies, bread, and chocolate; bakery mixes; processed meat products; frozen entrees; and frozen foods or the like.

EXAMPLES

Analysis Method (i) Measurement of MCPD-FS (in Accordance with Option A of Deutsche Gesellschaft für Fettwissenschaft (DGF) Standard Method C-III 18(09))

About 100 mg of an oil or fat sample was weighed in a test tube with a lid. 50 µL of an internal standard substance (3-MCPD-d5/t-butyl methyl ether), 500 μL of a t-butyl methyl ether/ethyl acetate-mixed solution (volume ratio 8:2), and 1 mL of 0.5 N sodium methoxide were added to the oil or fat sample, followed by stirring, and the resulting mixture was left to stand for 10 minutes. 3 mL of hexane and 3 mL of a 3.3% acetic acid/20% sodium chloride aqueous solution were added thereto, followed by stirring, and the upper layer of the resulting mixture was removed. 3 mL of hexane was further added, followed by stirring, and the upper layer of the resulting mixture was then removed. 250 μL of a mixed solution of 1 g of phenylboronic acid and 4 mL of 95% acetone were added, followed by stirring, and the test tube was hermetically sealed and heated at 80° C. for 20 minutes. 3 mL of hexane were added thereto, followed by stirring, and the upper layer of the resulting mixture was subjected to measurement with a gas chromatograph-mass spectrometer (GC-MS) to quantify MCPD-FS.

(ii) Glyceride Composition

About 10 mg of an oil or fat sample and 0.5 mL of a trimethylsilylating agent ("Silylating Agent TH" manufactured by Kanto Chemical Co., Inc.) were added into a glass sample bottle, followed by hermetical sealing, and the glass sample bottle was heated at 70° C. for 15 minutes. 1.0 mL of water and 1.5 mL of hexane were added to the mixture, followed by shaking. After leaving it to stand, the upper layer was subjected to gas-liquid chromatography (GLC) to perform analysis.

(iii) Constituent Fatty Acid Composition

A fatty acid methyl ester was prepared according to "Preparation method of fatty acid methyl ester (2.4.1.-1996)" in "Standard Methods for Analysis of Fats, Oils and Related Materials" edited by Japan Oil Chemists' Society. The resulting sample is measured by American Oil Chemists' Society. Official Method Ce 1f-96 (GLC method).

(iv) Content Ratio of Trans Isomers

Calculation was made on the basis of the fatty acids composition obtained as described above. The ratio of fatty acid having two double bonds including a trans double bond and having 18 carbon atoms (trans-linoleic acids) to fatty acid having two double bonds and having 18 carbon atoms (all linoleic acids) was expressed in terms of percentage. The ratio expressed in terms of percentage was defined as "content ratio (%) of trans isomers" (LTR).

(v) Hydroxyl value "Hydroxyl value (pyridine-acetic anhydride method 2.3.6.2-1996)" in "Standard Methods for the Analysis of Fats, Oils and Related Materials, 2003" edited by Japan Oil Chemists' Society About 5 g of an oil or fat sample was weighed in a round-bottom flask with a long neck. 5 ml of an acetylating reagent were added to the oil or fat sample and a small funnel was put in the neck of the flask. The bottom portion of the flask was immersed in a heating bath up to a depth of about 1 cm and was heated to a temperature of 95 to 100° C. One hour later, the flask was taken out from the heating bath and was then cooled. 1 ml of distilled water was added into the flask through the funnel, and the flask was heated again in the heating bath for 10 minutes. The flask was cooled again to normal temperature, and the liquid condensed on the inside surface of the funnel and on the inside surface of the neck of the flask was washed down into the flask with 5 ml of neutral ethanol. The resulting liquid was subjected to titration with a 0.5 mol/L of potassium hydroxide-ethanol standard solution by using a phenolphthalein indicator. Note that a blank test was performed simultaneously with the main test and a value calculated from the results of the titration on the basis of the following equation was defined as "hydroxyl value (mg-KOH/g)" (OHV).

$$\text{Hydroxyl value} = (A-B) \times 28.05 \times F/C + \text{acid value}$$

(A: Amount (ml) of a 0.5 mol/L of potassium hydroxide-ethanol standard solution used in a blank test, B: Amount (ml) of a 0.5 mol/L of potassium hydroxide-ethanol standard solution used in a main test, F: Factor of a 0.5 mol/L of potassium hydroxide-ethanol standard solution, and C: Collection amount (g) of a sample)

(Evaluation to Taste and Flavor)

The evaluation to a taste and flavor was performed by a panel of five members. Each member ate 1 to 2 g of each sample raw and performed a sensory evaluation based on the criteria shown below. The average value of the scores was shown. Note that when the average value of a sample is 4 or more, the sample is considered to be highly accepted by consumers.

5: A non-oily and light taste
4: A slightly oily and light taste
3: A slightly oily and rather light taste
2: An oily but rather light taste
1: An oily and heavy taste (Material Oil or Fat)

Oils or fats each having the composition shown in Table 1 were used as material oils or fats A to C.

TABLE 1

| | | Material oil or fat | | |
|---|---|---|---|---|
| Origin of oil or fat | | A<br>Rice germ oil | B<br>Vegetable oil | C<br>Corn oil |
| Glyceride composition [%] | MAG | 0.2 | 0.1 | 0.0 |
| | DAG | 7.8 | 7.7 | 2.5 |
| | TAG | 91.0 | 91.9 | 97.3 |
| | Fatty acids | 1.0 | 0.3 | 0.2 |
| Fatty acid composition [%] | C14:0 | 0.3 | 0.2 | 0.0 |
| | C16:0 | 16.8 | 11.6 | 10.7 |
| | C16:1 | 0.2 | 0.0 | 0.1 |
| | C18:0 | 1.8 | 1.8 | 2.0 |
| | C18:1 | 42.5 | 51.1 | 28.8 |
| | C18:2 | 35.3 | 28.9 | 56.1 |
| | C18:3 | 1.3 | 4.3 | 1.1 |
| | C20:0 | 0.7 | 0.7 | 0.5 |
| | C20:1 | 0.5 | 0.8 | 0.3 |
| | C22:0 | 0.2 | 0.3 | 0.2 |
| | C24:0 | 0.4 | 0.3 | 0.2 |

Examples 1 and 2

A Smith distiller was used as a thin-film evaporator to perform distillation of each of the material oils or fats A and B under the condition of a pressure of 4 Pa and a distillation temperature of 240° C., while supplying each of the oil or fat samples at a rate of 3 g per minute, yielding a treated oil. Next, the treated oil was brought into contact with the water vapor for 30 minutes under the condition of a pressure of 400 Pa, a treatment temperature of 180° C., and a mass ratio of water vapor/treated oil=0.1, yielding an oil or fat composition. Table 2 shows the analysis values thereof.

Comparative Examples 1, 3, and 5

Table 2 shows the analysis values in the case where the above-mentioned treatment in Example 1 or the like was not applied to each of the material oils or fats A to C.

Comparative Examples 2 and 4

Table 2 shows the analysis values in the case where the material oil or fat A or B was brought into contact with water vapor for 30 minutes under the condition of a pressure of 400 Pa, a treatment temperature of 180° C., and a mass ratio of water vapor/material oil or fat=0.1.

TABLE 2

|  | Example | | Comparative Example | | | | |
|---|---|---|---|---|---|---|---|
|  | 1 | 2 | 1 | 2 | 3 | 4 | 5 |
| Kind of material oil or fat | A | B | A | A | B | B | C |
| MCPD-FS (ppm) | 0.7 | 0.4 | 9.7 | 7.8 | 4.9 | 4.4 | 1.9 |
| OHV (mg-KOH/g) | 5.4 | 4.9 | 9.1 | 8.6 | 9.6 | 9.3 | 4 |
| LTR | 2.2 | 2.1 | 2.2 | 2.2 | 2.1 | 2.1 | 2.0 |
| Taste and flavor | 5 | 5 | 2 | 2 | 2 | 2 | 2 |

Examples 3 to 15 and Comparative Examples 6 and 7

A sucrose fatty acid ester (O-170, manufactured by Mitsubishi-Kagaku Foods Corporation) or a glycerin fatty acid monoester (O-95R, manufactured by Kao Corporation) was added to the material oil or fat A or B, yielding an oil or fat composition. Tables 3 and 4 show the analysis values thereof.

TABLE 3

|  | Example | | | | | | Comparative Example |
|---|---|---|---|---|---|---|---|
|  | 3 | 4 | 5 | 6 | 7 | 8 | 6 |
| Material oil or fat A (%) | 97.5 | 95.0 | 90.0 | 85.0 | 80.0 | 75.0 | 70.0 |
| Sucrose fatty acid ester (%) | 0.0 | 0.0 | 0.0 | 0.0 | 0.0 | 0.0 | 0.0 |
| Glycerin fatty acid monoester (%) | 2.5 | 5.0 | 10.0 | 15.0 | 20.0 | 25.0 | 30.0 |
| Total | 100.0 | 100.0 | 100.0 | 100.0 | 100.0 | 100.0 | 100.0 |
| MCPD-FS (ppm) | 9.4 | 9.2 | 8.7 | 8.2 | 7.7 | 7.2 | 6.8 |
| OHV (mg-KOH/g) | 18.2 | 25.7 | 40.5 | 56.5 | 70.3 | 87.5 | 100.4 |
| LTR | 2.2 | 2.2 | 2.3 | 2.4 | 2.5 | 2.6 | 2.7 |
| Taste and flavor | 4 | 5 | 5 | 5 | 5 | 4 | 2 |

TABLE 4

|  | Example | | | | | | | Comparative Example |
|---|---|---|---|---|---|---|---|---|
|  | 9 | 10 | 11 | 12 | 13 | 14 | 15 | 7 |
| Material oil or fat B (%) | 92.0 | 97.5 | 95.0 | 90.0 | 85.0 | 80.0 | 75.0 | 70.0 |
| Sucrose fatty acid ester (%) | 8.0 | 0.0 | 0.0 | 0.0 | 0.0 | 0.0 | 0.0 | 0.0 |
| Glycerin fatty acid monoester (%) | 0.0 | 2.5 | 5.0 | 10.0 | 15.0 | 20.0 | 25.0 | 30.0 |
| Total | 100.0 | 100.0 | 100.0 | 100.0 | 100.0 | 100.0 | 100.0 | 100.0 |
| MCPD-FS (ppm) | 4.8 | 4.8 | 4.7 | 4.4 | 4.2 | 3.9 | 3.7 | 3.5 |
| OHV (mg-KOH/g) | 13.2 | 18.6 | 26.1 | 41.0 | 56.9 | 70.8 | 88.0 | 100.8 |
| LTR | 2.0 | 2.1 | 2.1 | 2.2 | 2.2 | 2.3 | 2.5 | 2.5 |
| Taste and flavor | 4 | 4 | 5 | 5 | 5 | 4 | 4 | 2 |

As shown in Tables 2 to 4, each known oil or fat (each of Comparative Examples 1, 3, and 5), which had had a thermal history, had a heavy taste and flavor, and even though each oil or fat (each of Comparative Examples 2 and 4) had been produced by subjecting each known oil or fat to only deodorization treatment at a treatment temperature of 180° C. without subjecting it to distillation, the improvement of its heavy taste and flavor was not accomplished. Further, each oil or fat (each of Comparative Examples 6 and 7), which had a hydroxyl value (OHV) exceeding 88 mg-KOH/g, had a heavy taste and flavor.

In the meantime, if an oil or fat composition was produced so that its hydroxyl value (OHV) was controlled to 88 mg-KOH/g or less and its value was controlled to a value larger than the one calculated by substituting its MCPD-FS content into the above-mentioned expression (1), the oil or fat composition was not oily and had a very good taste and flavor.

The invention claimed is:

1. An oil or fat composition, comprising linoleic acid, wherein the oil or fat composition satisfies expression (1):

$$Y \geq 1.25X + 4 \text{ where } Y \leq 88 \qquad (1),$$

wherein X is an MCPD-FS content (ppm), which is a total content in the oil or fat composition of 3-chloropropane-1,2-diol, esters of 3-chloropropane-1,2-diol, glycidol, and esters of glycidol, as measured by a Deutsche Gesellschaft für Fettwissenschaft (DGF) standard method C-III 18(09), wherein Y is a hydroxyl value of the oil or fat composition in mg-KOH/g, and wherein the linoleic acid has a content (%) of trans isomers of linoleic acids in constituent fatty acids of an oil or fat, of 2% or more.

2. The oil or fat composition according to claim 1, wherein Y is 4.9 to 88 mg-KOH/g.

3. The oil or fat composition according to claim 1, wherein Y is 19 to 87 mg-KOH/g.

4. The oil or fat composition according to claim 1, wherein the oil or fat composition satisfies expression (2):

$$Y \geq 2X + 4 \text{ where } Y \leq 70.5 \qquad (2).$$

5. The oil or fat composition according to claim 1, wherein Y is 26 to 70 mg-KOH/g.

6. The oil or fat composition according to claim 1, wherein X is 10 ppm or less.

7. The oil or fat composition according to claim 1, wherein X is 9 ppm or less.

8. The oil or fat composition according to claim 1, wherein X is 5 ppm or less.

9. The oil or fat composition according to claim 1, wherein X is 0.1 to 5 ppm.

10. The oil or fat composition according to claim 1, wherein X is 0.4 to 4.7 ppm.

11. The oil or fat composition according to claim 1, which has a content ratio (%) of trans isomers of linoleic acids in constituent fatty acids of an oil or fat, of 2 to 8.

12. The oil or fat composition according to claim 1, which has a content ratio (%) of trans isomers of linoleic acids in constituent fatty acids of an oil or fat, of 2 to 5.

13. The oil or fat composition according to claim 1, which has a content ratio (%) of trans isomers of linoleic acids in constituent fatty acids of an oil or fat, of 2.1 to 5.

14. The oil or fat composition according to claim 1, which has a content ratio (%) of trans isomers of linoleic acids in constituent fatty acids of an oil or fat, of 2.1 to 2.6.

15. The oil or fat composition according to claim 1, which has a content of triacylglycerol of 49.8 to 95.8 mass %.

16. The oil or fat composition according to claim 15, which has a content of diacylglycerol of 4 to 50 mass %.

17. The oil or fat composition according to claim 1, which has a content of triacylglycerol of 75 to 94.5 mass %.

18. The oil or fat composition according to claim 17, which has a content of diacylglycerol of 5 to 20 mass %.

19. The oil or fat composition of claim 1, wherein the oil or fat composition is obtained by a refining process comprising a deodorizing step in which the oil or fat is treated at a temperature of 120 to 230° C. for 1 to 110 minutes.

* * * * *